(12) United States Patent
Mrazek

(10) Patent No.: US 10,435,746 B2
(45) Date of Patent: Oct. 8, 2019

(54) METHODS FOR SELECTING MEDICATIONS FOR TREATING PATIENTS HAVING ATTENTION-DEFICIT HYPERACTIVITY DISORDER

(75) Inventors: David A. Mrazek, Rochester, MN (US); Patricia J. Mrazek, legal representative, Rochester, MN (US)

(73) Assignee: MAYO FOUNDATION FOR MEDICAL EDUCATION AND RESEARCH, Rochester, NY (US)

( * ) Notice: Subject to any disclaimer, the term of this patent is extended or adjusted under 35 U.S.C. 154(b) by 98 days.

(21) Appl. No.: 13/880,694

(22) PCT Filed: Oct. 20, 2011

(86) PCT No.: PCT/US2011/057007
§ 371 (c)(1),
(2), (4) Date: Aug. 29, 2013

(87) PCT Pub. No.: WO2012/054681
PCT Pub. Date: Apr. 26, 2012

(65) Prior Publication Data
US 2014/0024029 A1 Jan. 23, 2014

Related U.S. Application Data

(60) Provisional application No. 61/405,272, filed on Oct. 21, 2010.

(51) Int. Cl.
| C12Q 1/68 | (2018.01) |
| C12P 19/34 | (2006.01) |
| C12Q 1/6883 | (2018.01) |
| G01N 33/68 | (2006.01) |
| G16B 20/00 | (2019.01) |

(52) U.S. Cl.
CPC ....... *C12Q 1/6883* (2013.01); *G01N 33/6893* (2013.01); *G16B 20/00* (2019.02); *C12Q 2600/106* (2013.01); *C12Q 2600/156* (2013.01); *G01N 2800/305* (2013.01); *G01N 2800/52* (2013.01)

(58) Field of Classification Search
CPC ........ C12Q 2600/106; C12Q 2600/156; C12Q 2600/136; C12Q 2600/112; G06F 19/18; G06F 19/28; G06F 19/3456; G06F 19/24; G06Q 50/24; G01N 2800/305; G01N 2800/52; G01N 33/6893
See application file for complete search history.

(56) References Cited

U.S. PATENT DOCUMENTS

| 7,795,033 B2 | 9/2010 | McMahon et al. |
| 8,355,927 B2 | 1/2013 | Lombard |
| 2002/0091664 A1 | 7/2002 | Larder et al. |
| 2006/0204961 A1 | 9/2006 | Swanson et al. |
| 2008/0020387 A1 | 1/2008 | Lawrence |
| 2008/0311563 A1 | 12/2008 | Mrazek et al. |
| 2009/0253617 A1 | 10/2009 | Kim et al. |
| 2010/0143921 A1 | 6/2010 | Sadee et al. |

FOREIGN PATENT DOCUMENTS

| JP | 2007-525154 A | 9/2007 |
| WO | WO-2004/074456 A2 | 9/2004 |
| WO | WO-2004/074456 A3 | 9/2004 |

OTHER PUBLICATIONS

Ramoz N. et al. Neuropsychopharmacology (2009) 34, 2135-2142.*
DbSNP Reference SNP (refSNP) Cluster Report: rs4646894, 2 oages printed on Sep. 14, 2017 from www.ncbi.nlm.nih.gov.*
D'Souza et al. "Functional Effects of a Tandem Duplication Polymorphism in the 5'Flanking Region of the DRD4 Gene." *Biol. Psychiatry.* 56.9(2004):691-697.
Froehlich et al. "Progress and Promise of Attention-Deficit Hyperactivity Disorder Pharmacogenetics." *CNS Drugs.* 24.2(2010):99-117.
Guatelli et al. "Isothermal, in vitro Amplification of Nucleic Acids by a Multienzyme Reaction Modeled After Retroviral Replication." *PNAS.* 87.5(1990):1874-1878.
Lewis. "PCR's Competitors are Alive and Well and Moving Rapidly Towards Commercialization." *Genetic Engineering News.* 12.9(1992):1, 8-9.
Lovejoy et al. "The Serotonin Transporter Intronic VNTR Enhancer Correlated with a Predisposition to Affective Disorders has Distinct Regulatory Elements Within the Domain Based on the Primary DNA Sequence of the Repeat Unit." *Eur. J. Neurosci.* 17.2(2003):417-420.
McGough et al. "A Candidate Gene Analysis of Methylphenidate Response in Attention-Deficit/Hyperactivity Disorder." *J. Am. Acad. Child Adolesc. Psychiatry.* 48.12(2009):1155-1164.
Myakishev et al. "High-Throughput SNP Genotyping by Allele-Specific PCR with Universal Energy-Transfer-Labeled Primers." *Genome Res.* 11.1(2001):163-169.
Prince et al. "Robust and Accurate Single Nucleotide Polymorphism Genotyping by Dynamic Allele-Specific Hybridization (DASH): Design Criteria and Assay Validation." *Genome Res.* 11.1(2001):152-162.
Stoneking et al. "Population Variation of Human mtDNA Control Region Sequences Detected by Enzymatic Amplification and Sequence-Specific Oligonucleotide Probes." *Am. J. Hum. Genet.* 48.2(1991):370-382.
Weiss. "Hot Prospect for New Gene Amplifier." *Science.* 254. 5036(1991):1292-1293.
Contini et al. "Pharmacogenetics of Response to Methylphenidate in Adult Patients with Attention-Deficit/Hyperactivity Disorder (AD/HD): A Systematic Review." *Eur. Neuropharmacol.* 23.6(2013):555-560.

(Continued)

*Primary Examiner* — Stephen T Kapushoc
(74) *Attorney, Agent, or Firm* — Muriel Liberto, Esq.; Mintz Levin Cohn Ferris Glovsky and Popeo, P.C.

(57) ABSTRACT

Methods for selecting a medication for a patient are described that include determining the patient's genotype for a panel of genes, identifying a phenotype associated with the genotype for each gene, and selecting the medication based on the phenotype.

9 Claims, 2 Drawing Sheets

(56) References Cited

OTHER PUBLICATIONS

Polanczyk et al. "Pharmacogenetic Approach for a Better Drug Treatment in Children." *Curr. Pharma. Des.* 16.22(2010):2462-2473.
Sonuga-Barke et al. "Does Parental Expressed Emotion Moderate Genetic Effects in ADHD? An Exploration Using a Genome Wide Association Scan." *Am. J. Med. Genet. Part B.* 147B.8(2008):1359-1368.

* cited by examiner

METHODS FOR SELECTING MEDICATIONS FOR TREATING PATIENTS HAVING ATTENTION-DEFICIT HYPERACTIVITY DISORDER

CROSS-REFERENCE TO RELATED APPLICATION

This application is a National Stage application under 35 U.S.C. § 371 of International Application No. PCT/US2011/057007, having an International Filing Date of Oct. 20, 2011, which claims the benefit of U.S. Provisional Application No. 61/405,272, filed Oct. 21, 2010. The disclosure of the foregoing application is hereby incorporated by reference in its entirety.

TECHNICAL FIELD

This document relates to methods for selecting a medication for treating a patient having Attention Deficit Hyperactivity Disorder (ADHD), and more particularly to selecting a patient's medication based on the genotype of genes encoding drug-metabolizing enzymes and genes encoding products involved in, for example, neurotransmission.

SUMMARY

This document is based on the identification of a set of genes with polymorphisms that are associated with ADHD and pharmacological response to a medication. As a result, methods of the invention allow the genotype of a patient to be determined and, based on the phenotype associated with the genotype, a suitable medication to be selected for the patient having ADHD. Methods of the invention allow the output of multiple genotypic assessments to be integrated, providing important and improved clinical information on which to select and dose medications. Thus, the methods of the invention provide a rational method for the identification of a medication that will result in an optimal response in the patient.

In one aspect, this document features a method for selecting a medication for a patient having ADHD. The method includes providing a biological sample (e.g., peripheral blood sample or saliva) from a patient; obtaining, from the biological sample, the patient's genotype for a panel of genes, wherein the panel includes a cytochrome P450 2D6 (CYP2D6) gene, a catechol-O-methyl transferase (COMT) gene, norepinephrine transporter gene SLC6A2, dopamine transporter gene SLC6A3, and dopamine receptor gene DRD4; identifying a phenotype associated with the patient's genotype of each gene within the panel of genes; combining each phenotype into a combined phenotype for the patient; and selecting the medication based on the patient's combined phenotype. Selecting the medication can include ranking medications based on the patient's combined phenotype. Obtaining the patient's genotype for CYP2D6 can include determining if the patient comprises the CYP2D6*1A, 2D6*2, 2D6*2N, 2D6*3, 2D6*4, 2D6*5, 2D6*6, 2D6*7, 2D6*8, 2D6*10, 2D6*12, or 2D6*17 allele. In some embodiments, obtaining the patient's genotype for CYP2D6 can include determining if the patient comprises the CYP2D6*1A, *2A, *2B, *2N, *3, *4, *5, *6, *7, *8, *9, *10, *11, *12, *15, *17,*35, or *41 allele. The panel of genes further can include serotonin transporter gene SLC6A4, an ADRA2A gene encoding the alpha-2A adrenergic receptor, a SNAP25 gene encoding synaptosomal-associated protein 25, and/or the SLC1A1 gene encoding the neuronal glutamate transporter. The medication can be a methylphenidate, an amphetamine (e.g., a long acting amphetamine or a short acting amphetamine), or atomoxetine. The long acting amphetamine can be selected from the group consisting of a dextroamphetamine spansule preparation, an extended release amphetamine salt preparation, and a lisdexamphetamine preparation. The short acting amphetamine can be selected from the group consisting of dextroamphetamine sulfate preparation, an amphetamine salt preparation of dextroamphetamine and amphetamine, and methamphetamine.

In another aspect, this document features a method of selecting a medication for a patient having ADHD. The method includes receiving, in a computer system, a patient's genotype for a panel of genes, wherein the panel includes a CYP2D6 gene, a COMT gene, norepinephrine transporter gene SLC6A2, dopamine transporter gene SLC6A3, and dopamine receptor gene DRD4, wherein the computer system includes a listing of a plurality of medications suitable for treating ADHD; identifying, using the computer system, a phenotype associated with the genotype of each gene within the panel of genes; combining, using the computer system, each phenotype into a combined phenotype for the patient; selecting one or more medications for treating the patient by quantitatively considering each phenotype of the combined phenotype; and outputting the selected medication or medications from the computer system. The patient's genotype can be received directly from equipment used in determining the patient's genotype. In some embodiments, a user enters the patient's genotype in the computer system. The method further can include before the outputting step, ranking, using the computer system, the selected medications based on the patient's combined phenotype.

This document also features a non-transitory computer readable medium containing executable instructions that when executed cause a processor to perform operations comprising receive a patient's genotype for a panel of genes, wherein the panel of genes comprises a CYP2D6 gene, a COMT gene, norepinephrine transporter gene SLC6A2, dopamine transporter gene SLC6A3, and dopamine receptor gene DRD4; identify a phenotype associated with the genotype for each gene within the panel of genes; combine each phenotype into a combined phenotype for the patient; identify, in a database including a plurality of medications suitable for treating ADHD, a medication that is associated with the patient's combined phenotype; and output the identified medication in response to receiving the patient's genotype.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the description and drawings, and from the claims.

DETAILED DESCRIPTION

Figure 1:
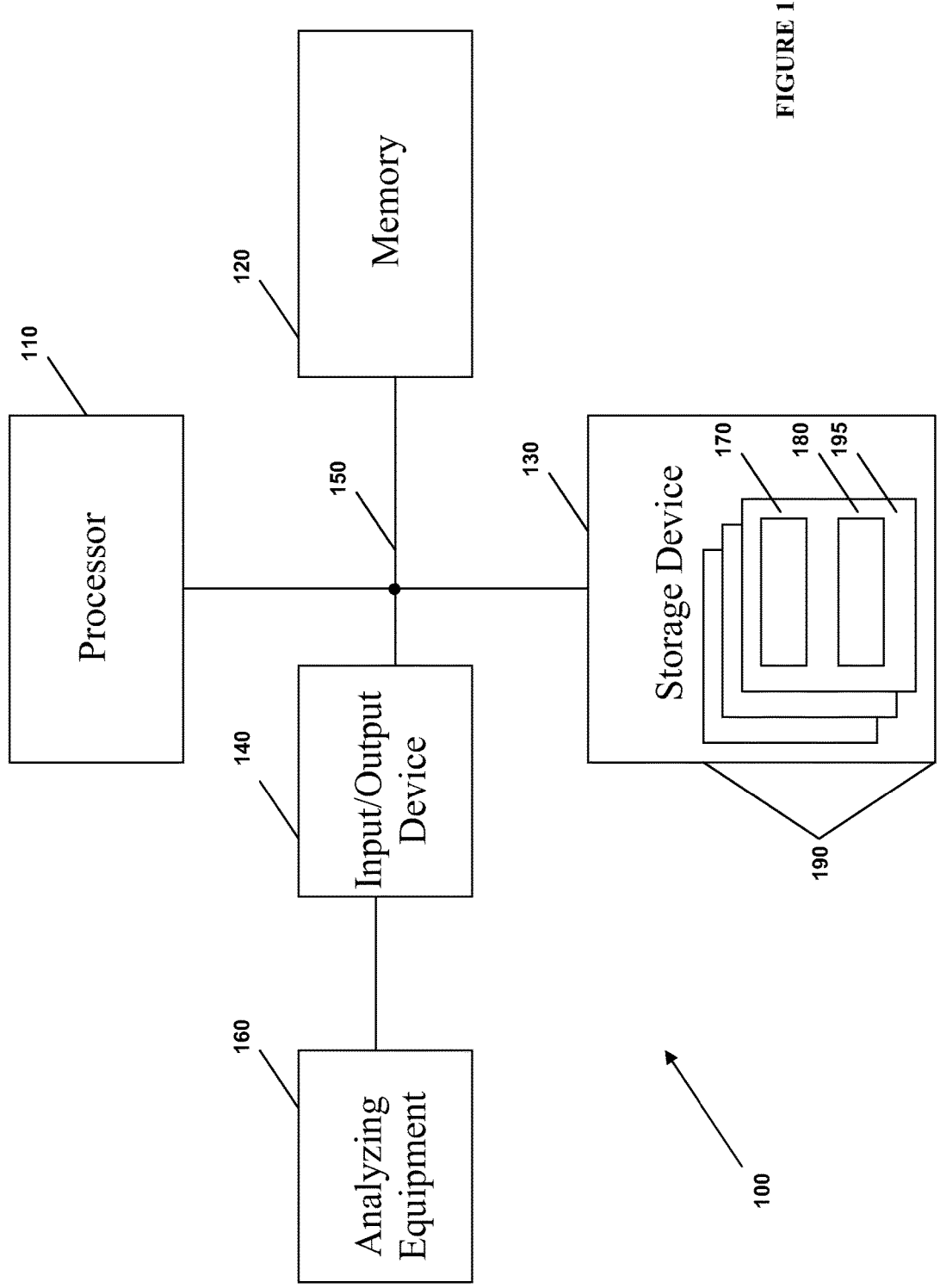
FIG. 1 is a block diagram of a computer system 100, according to one embodiment.

In general, the invention features a method for selecting a medication for treating a patient having ADHD based on the genotype of genes that are useful for medication selection. Genes to be genotyped typically encode products that influence the metabolism of a medication or that are associated with differential response. An algorithm can be used that initially assigns a phenotype associated with the patient's genotype for each gene within the panel, and then combines each phenotype into a combined phenotype for the patient. A series of rules then can be applied to select an appropriate medication based on the combined phenotype.

Medications useful for treating ADHD include psychostimulants (e.g., methylphenidates and amphetamines) and nonstimulants (e.g., atomoxetine (Strattera), a selective norepinephrine reuptake inhibitor). Non-limiting examples of methyphenidates include short-acting, intermediate-acting, and long-acting preparations. For example, short-acting preparations of methylphenidate hydrochloride (e.g., d,l-methylphenidate such as Ritalin or Methylin), intermediate acting (also referred to as extended release (ER) or sustained release (SR)) methylphenidate hydrochloride preparations such as Ritalin SR, Methylin ER, and Metadate ER, or long-acting (LA) methylphenidate preparations such as methyphenidate osmotic oral release system (OROS) (Concerta), Metadate controlled delivery (CD), Ritalin LA, or the methylphenidate transdermal patch (Daytrana). Non-limiting examples of amphetamines include short-acting and long-acting preparations. For example, a short-acting amphetamine preparation can be a dextroamphetamine sulfate preparation (e.g., Dexedrine or Dextrostat), an amphetamine salt preparation of the neural sulfate salts of dextroamphetamine and amphetamine (e.g., Adderall), a methamphetamine hydrochloride preparation (e.g., Desoxyn), or a dexmethylphenidate hydrochloride preparation (d-methylphenidate, e.g., Focalin). A long-acting amphetamine preparation can be a dextroamphetamine spansule preparation (e.g., Dexedrin Spansules), an ER amphetamine salt preparation (e.g., Adderall XR), or lisdexamfetamine dimesylate (a prodrug metabolized to dextroamphetamine, e.g., Vyvanse).

Genomic testing of a plurality of genes encoding drug metabolizing enzymes (e.g. cytochrome P450 D6) and other target genes (e.g., genes involved in neurotransmission) provides a safe method by which potentially dangerous side effects can be avoided in an affected patient.

Panels of Genes

The method includes obtaining a biological sample from a patient and obtaining the patient's genotype for a panel of genes. Typically, the panel of genes that are genotyped includes a cytochrome P450 gene such as CYP2D6 and a plurality of target genes that encode products that relate to the ability of the patient to respond to a particular class of medication. For example, the plurality of target genes can be a gene encoding catechol-O-methyl transferase (COMT), a gene encoding a norepinephrine transporter (e.g., SLC6A2) a gene encoding a dopamine transporter (e.g., SLC6A3), and a gene encoding a dopamine receptor (e.g., DRD4). As such, in one embodiment, the panel of genes can be the CYP2D6 gene, COMT gene, and SLC6A2 gene, SLC6A3 gene, and DRD4 gene. Alleles for each of these genes are set forth in Table 1.

Substrates of CYP2D6 typically are weak bases with the cationic binding site located away from the carbon atom to be oxidized. In particular, substrates of CYP2D6 include atomoxetine and amphetamines. Some individuals have altered CYP2D6 gene sequences that result in synthesis of enzymes devoid of catalytic activity or in enzymes with diminished catalytic activity. Duplication of the functional CYP2D6 gene also has been observed and results in ultrarapid metabolism of drugs. Individuals without inactivating polymorphisms, deletions, or duplications have the phenotype of an extensive drug metabolizer and are designated as CYP2D6*1. The CYP2D6*2 allele has decreased enzymatic activity resulting from amino acid substitutions. The CYP2D6*3 and *4 alleles account for nearly 70% of the total deficiencies that result in the poor metabolizer phenotype. The polymorphism responsible for CYP2D6*3 (2549A>del) produces a frame-shift in the mRNA. A polymorphism involved with the CYP2D6*4 allele (1846G>A) disrupts mRNA splicing. These changes produce truncated forms of CYP2D6 devoid of catalytic activity. Other poor metabolizers are CYP2D6*5, *10, and *17. CYP2D6*5 is due to complete gene deletion. The polymorphisms in CYP2D6*10 and *17 produce amino acid substitutions in the CYP2D6 enzyme which have decreased enzyme activity. All of these polymorphisms are autosomal recessive. Consequently, only individuals who are homozygous or who are compound heterozygous for these polymorphisms are poor metabolizers. Individuals who are heterozygous, with one normal gene and one polymorphic gene, will have metabolism intermediate between the extensive (normal) and poor metabolizers. As used herein, patients are identified as having phenotype 1 if they are a poor or ultra-rapid metabolizer, phenotype 2 if they are an intermediate metabolizer, and phenotype 3 if they are an extensive metabolizer. Table 2 lists the CYP2D6 alleles and the associated activity.

TABLE 1

| Name | Symbol or Allele | Polymorphism |
| --- | --- | --- |
| CYP2D6 | *1A | None |
|  | *2A | C-1584G, G1661C, C2850T, G4180C |
|  | *2B | G1661C, C2850T, G4180C |
|  | *2N | Gene duplication |
|  | *3 | A2549 deletion |
|  | *4 | G1846A, C100T, G1661C, G4180C |
|  | *5 | Gene deletion |
|  | *6 | T1707 deletion |
|  | *7 | A2935C |
|  | *8 | G1661C, G1758T, C2850T, G4180C |
|  | *9 | A2613 deletion, A2614 deletion, G2615 deletion |
|  | *10 | C100T, G1661C, G4180C |
|  | *11 | G883C, G1661C, C2850T, G4180C |
|  | *12 | G124A, G1661C, C2850T, G4180C |
|  | *15 | T138 insertion |
|  | *17 | C1023T, G1661C, C2850T, G4180C |
|  | *35 | G31A |
|  | *41 | C-1584G, R296C, S486T, G1661C, C2850T, G2988A, G4180C |
| Dopamine Transporter | DAT1, SLC6A3 | 40 bp VNTR 10 repeat allele G710A, Q237R C124T, L42F |
| Dopamine Receptor D1 | DRD1 | DRD1 B2 T244G C179T G127A T11G C81T T595G, S199A G150T, R50S |

TABLE 1-continued

| Name | Symbol or Allele | Polymorphism |
|---|---|---|
| | | C110G, T37R |
| | | A109C, T37P |
| Dopamine Receptor D2 | DRD2 | TaqI A |
| | | A1051G, T35A |
| | | C932G, S311C |
| | | C928, P310S |
| | | G460A, V154I |
| Dopamine Receptor D3 | DRD3 | BalI in exon I |
| | | MspI |
| | | DRD3 1 |
| | | Gly/Ser (allele 2) |
| | | A25G, S9G |
| Dopamine Receptor D4 | DRD4 | 240 polymorphism in promoter region (+240/+240; +240/−240; or −240/−240); 48 repeat in exon 3 |
| | | 7 repeat allele |
| | | 12/13 bp insertion/deletion |
| | | T581G, V194G |
| | | C841G, P281A |
| Dopamine Receptor D5 | DRD5 | T978C |
| | | L88F |
| | | A889C, T297P |
| | | G1252A, V418I |
| | | G181A, V61M |
| | | G185C, C62S |
| | | T263G, R88L |
| | | G1354A, W455 |
| Serotonin Transporter | 5-HTTR SLC6A4 | Promoter repeat (44 bp insertion (L)/deletion(S) (L = Long form; S = Short form); Intron 2 variable number of repeats (9, 10, 11, or 12); A1815C; G603C; G167C; −3745, T→A (5'FR); −3636, T→C (5'FR); −3631 G→A (5'FR); SNP rs25531, A→G (5'FR); −1090, A→T (5'FR); −1089, A→T (5'FR); −859, A→C (5'FR); −482, T→C (5'FR); −469, C→T (5'FR); −45, C→A (intron 1A); −25, G→A intron 1A; −185, A→C (5' UTR); −149, C→A (5' UTR); G28A (intron 1b); T303C (exon 2); −100, G→A (intron 4); C83T (intron 7); C1149T (exon 8); T204G (intron 8); −131, C→T (intron 11) |
| Catechol-o-methyl-transferase | COMT | G158A (Also known as Val/Met) |
| | | G214T |
| | | A72S |
| | | G101C |
| | | C34S |
| | | G473A |
| Synaptosomal-associated protein 25 | SNAP25 | T1069C |
| | | T1065G |
| Neuronal Glutamate transporter | SLCA1A | Reference SNP (rs) 2228622 rs3780412 |
| Norepinephrine Transporter Protein 1 | SLC6A2 | G1278A (exon 9) |
| | | 36001 A/C |
| | | 28257 G/C |
| | | 28323C/T |
| | | 4 bp insertion/deletion polymorphism in promoter |
| Adrenergic alpha 2A receptor | ADRA2A | −1291 C > G |

TABLE 2

| CYP2D6 Alleles and Associated Activity | |
|---|---|
| Allele | Activity Level |
| *1 | normal |
| *2A | increased |
| *2BD | decreased |
| *3 | none |
| *4 | none |
| *5 | none |
| *6 | none |
| *7 | none |
| *8 | none |
| *9 | decreased |
| *10 | decreased |
| *11 | none |
| *12 | none |
| *15 | none |
| *17 | decreased |
| *35 | increased |
| *41 | decreased |

A tandem duplication polymorphism in the promoter of the DRD4 gene that comprises a 120-base-pair repeat sequence is known to have different allele frequencies in various populations around the world. See, D'Souza et al., Biol Psychiatry. 56(9):691-7 (2004). This polymorphism in the promoter region of DRD4 is associated with improved performance in solving math problems when subjects are given higher doses of methylphenidate. The official designation of this variant is rs4646984. The more common form of rs4646984 is the "240 nucleotide allele". The less common allele is the "120 nucleotide allele" and this shorter allele has been reported to have higher transcription activity. See, D'Sousa et al., 2004, supra. Children who are homozygous for the more active 120-repeat allele performed better on math testing than those children who had one or two copies of the less active 240-repeat allele when they were treated with doses of methylphenidate that were greater than 10 mg given three times a day.

A COMT polymorphism (Val158Met) has been associated with response to amphetamine. In particular, working memory efficiency was enhanced by amphetamine administration for the val/val genotype (high COMT activity) while amphetamine produced adverse effects under high working memory load conditions for the met/met genotype (low activity). See, Froehlich et al., CNS Drugs, 24(2):99-117 (2010). Irritability and somatic symptoms in response to methylphenidate also are associated with this COMT polymorphism. See, McCough et al., J. Am. Acad. Child Adolesc. Psychiatry, 48(12):1155-1164 (2009).

Response to methylphenidate also is associated with a variable number of tandem repeats (VNTR) polymorphism in the 3' untranslated region of the SLC6A3 gene. There are at least 10 variations based on the number of tandem repeats in this unit. The 10 repeat unit is one of the more active common variants, and has been reported to be associated with an increased risk of ADHD. An improved methylphenidate response has been observed for 10-repeat homozygotes while 9-repeat homozygosity was associated with a diminished parent-rated medication response. Individuals homozygous for the 9-repeat allele also were less able to feel amphetamine effects relative to other genotypes. See, Froehlich et al., 2010, supra.

Stimulant medications block reuptake at norepinephrine transporters. Several polymorphisms in the SCL6A2 gene have been associated with ADHD and response to amphetamine and methylphenidate. For example, individuals homozygous for the A/A genotype at 1278 in exon 9 had decreased response to methylphenidate with respect to hyperactive-impulsive behaviors but not inattentive symptoms compared with the G/A or G/G phenotypes. With respect to amphetamines, a C/C genotype at 36001 A/C, and the haplotype GCC from 28257 G/C, 28323 C/T, and 36001 A/C were associated with higher self-reported positive mood after amphetamine administration. These polymorphisms are located in transcription binding sites. See, Froehlich et al., 2010, supra.

In some embodiments, the panel of genes further can include one or more of the following: serotonin transporter gene SLC6A4, a gene encoding SNAP25, a gene encoding the alpha-2A adrenergic receptor (ADRA2A), a gene encoding the glutamate transporter (SLC1A1), a gene encoding carboxylesterase 1 (CES1), a gene encoding corticotropin-releasing hormone (CRH), and a gene encoding tryptophan hydroxylase 2 (TPH2). In one embodiment, a SLC6A4 gene is included on the panel with the CYP2D6, COMT, SLC6A2, SLC6A3, and DRD4 genes. In one embodiment, a SNAP25 gene is included on the panel with the CYP2D6, COMT, SLC6A2, SLC6A3, and DRD4 genes. In one embodiment, an ADRA2A gene is included on the panel with the CYP2D6, COMT, SLC6A2, SLC6A3, and DRD4 genes. In one embodiment, a SLC6A4 gene and a SNAP25 gene are included on the panel with the CYP2D6, COMT, SLC6A2, SLC6A3, and DRD4 genes. In one embodiment, a SLC6A4 gene and a ADRA2A gene are included on the panel with the CYP2D6, COMT, SLC6A2, SLC6A3, and DRD4 genes. In one embodiment, a SNAP25 gene and an ADRA2A gene are included on the panel with the CYP2D6, COMT, SLC6A2, SLC6A3, and DRD4 genes. In one embodiment, a SLC6A4 gene, a SNAP25 gene, and an ADRA2A gene are included on the panel with the CYP2D6, COMT, SLC6A2, SLC6A3, and DRD4 genes.

Children with different forms of a VNTR polymorphism located in the second intron of the SLC6A4 gene (see Table 1) respond differently to treatment with methylphenidate. The most common variant is the "12 repeat" allele, while the "9 repeat" allele is relatively rare. Animal studies indicate that the 12-repeat allele may up-regulate the function of the gene in comparison to the 10-repeat allele (Lovejoy et al, *Eur. J. Neurosci.* 17:417-420 (2003). Therefore, individuals with two copies of the 12-repeat may have the most active transcription of the serotonin transporter product, whereas those with two copies of 10-repeat allele may have a lower production of the serotonin transporter. As such, the 12-repeat genotype is associated with a better clinical response to methylphenidate.

Response to methylphenidate also has been associated with SNAP25, a neuron specific vesicle docking protein involved in neurotransmitter exocytosis from storage vesicles into the synaptic space. In particular, an association has been found between the T1065G and T1069C polymorphisms (see Table 1) and ADHD. Homozygotes for the T allele of T1065G have moderately improved methylphenidate dose responses while those homozygous for T at T1069C exhibit poor methylphenidate responses. Children homozygous for the G allele at 1065 were 2-3 times more likely to develop sleep difficulties and irritability than those with at least one copy of the T allele. Those homozygous for the C allele at 1069 were 2-4 times more likely to develop tics and other abnormal movements compared with T allele carriers. See, Froehlich et al., 2010, supra; and McCough et al., 2009, supra.

The alpha-2A adrenergic receptor (ADRA2A) is a norepinephrine autoreceptor that dampens the cell firing rate and limits norepinephrine release when activated. See, Froehlich et al., 2010, supra. Subjects having the less common G allele at −1291 (see Table 1) have improved methyphenidate response on inattention scores but not hyperactive-impulsive scores.

As described herein, an algorithm has been created based on a set of rules relating to the genotype of the five genes on the panel (e.g., CYP2D6 gene, the COMT gene, SLC6A2 gene, SLC6A3 gene, and DRD4 gene). An algorithm also can be used based on a set of rules relating to six genes (e.g., CYP2D6 gene, the COMT gene, SLC6A2 gene, SLC6A3 gene, DRD4 gene, and one of SLC6A4 gene, a SNAP25 gene, and an ADRA2A gene). Similarly, an algorithm can be used based on a set of rules relating to seven or eight genes (e.g., CYP2D6 gene, the COMT gene, SLC6A2 gene, SLC6A3 gene, DRD4 gene, and two or three of SLC6A4 gene, a SNAP25 gene, and an ADRA2A gene). Based on these algorithms, a medication or ranking of medications are provided for a given patient based on the patient's genotype, allowing a clinician to select an acceptable treatment for the patient with ADHD without the trial and error of determining if the patient will respond or tolerate a particular medication.

Determining Genotype

Genomic DNA generally is used to determine genotype, although mRNA also can be used. Genomic DNA is typically extracted from a biological sample such as a peripheral blood sample, but can be extracted from other biological samples, including saliva or tissues (e.g., mucosal scrapings of the lining of the mouth or from renal or hepatic tissue). Routine methods can be used to extract genomic DNA from a blood, saliva or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega) and the A.S.A.P.™ Genomic DNA isolation kit (Boehringer Mannheim, Indianapolis, Ind.).

Typically, an amplification step is performed before proceeding with the genotyping. For example, polymerase chain reaction (PCR) techniques can be used to obtain amplification products from the patient. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, Ed. by Dieffenbach, C. and Dveksler, G., Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication or nucleic acid sequence-based amplification also can be used to obtain isolated nucleic acids. See, for example, Lewis (1992) *Genetic Engineering News* 12(9):1; Guatelli et al. (1990) *Proc. Natl. Acad. Sci. USA* 87:1874-1878; and Weiss (1991) *Science* 254:1292-1293.

Primers typically are single-stranded or double-stranded oligonucleotides that are 10 to 50 nucleotides in length, and when combined with mammalian genomic DNA and subjected to PCR conditions, is capable of being extended to produce a nucleic acid product corresponding to a region of interest within a gene. Typically, PCR products are at least 30 nucleotides in length (e.g., 30, 35, 50, 100, 250, 500, 1000, 1500, or 2000 or more nucleotides in length). Specific regions of mammalian DNA can be amplified (i.e., replicated such that multiple exact copies are produced) when a pair of oligonucleotide primers is used in the same PCR reaction, wherein one primer contains a nucleotide sequence from the coding strand of a nucleic acid and the other primer contains a nucleotide sequence from the non-coding strand of the nucleic acid. The "coding strand" of a nucleic acid is the nontranscribed strand, which has the same nucleotide sequence as the specified RNA transcript (with the exception that the RNA transcript contains uracil in place of thymidine residues), while the "non-coding strand" of a nucleic acid is the strand that serves as the template for transcription.

A single PCR reaction mixture may contain one pair of oligonucleotide primers. Alternatively, a single reaction mixture may contain a plurality of oligonucleotide primer pairs, in which case multiple PCR products can be generated (e.g., 5, 10, 15, or 20 primer pairs). Each primer pair can amplify, for example, one exon or a portion of one exon. Intron sequences also can be amplified.

Exons or introns of a gene of interest can be amplified then directly sequenced. Dye primer sequencing can be used to increase the accuracy of detecting heterozygous samples. Alternatively, one or more of the techniques described below can be used to determine genotype.

For example, allele specific hybridization can be used to detect sequence variants, including complete haplotypes of a mammal. See, Stoneking et al., 1991, *Am. J. Hum. Genet.* 48:370-382; and Prince et al., 2001, *Genome Res.*, 11(1): 152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate (e.g., in discrete regions).

Allele-specific restriction digests can be performed in the following manner. For nucleotide sequence variants that introduce a restriction site, restriction digest with the particular restriction enzyme can differentiate the alleles. For sequence variants that do not alter a common restriction site, mutagenic primers can be designed that introduce a restriction site when the variant allele is present or when the wild type allele is present. A portion of the nucleic acid of interest can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of a gene of interest can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine). Amplification products can be analyzed for green and red fluorescence in a plate reader. See, Myakishev et al., 2001, *Genome* 11(1):163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Kits also are available commercially to detect many of the cytochrome P450 variants. For example, TAG-IT™ kits are available from Tm Biosciences Corporation (Toronto, Ontario).

Selecting Medications

After the genotype is determined for each gene on the panel, the medication can be selected. Typically, selecting includes correlating the genotype of the CYP2D6 with capacity of the enzyme to metabolize the medication, i.e., a phenotype is assigned based on the genotype. For example, patients are identified as having phenotype 1 if they are a poor or ultra-rapid metabolizer. Patients are identified as having phenotype 2 if they are an intermediate metabolizer or phenotype 3 if they are an extensive metabolizer.

The genotype of other target genes on the panel, e.g., the COMT gene, SLC6A2 gene, SLC6A3 gene, DRD4 gene, can be correlated with the ability of the patient to respond to the medication, i.e., a phenotype is assigned based on the genotype. For example, with respect to DRD4, patients are identified as having a positive phenotype if they have the 120 allele and are identified as having a negative phenotype if they have the 240 allele. For SLC6A3, patients are identified as having a positive phenotype if they have the 10 repeat unit and identified as having a negative phenotype if they have the 9 repeat unit. For SLC6A2, patients are identified as having a positive phenotype if they have G/A or G/G genotypes and a negative phenotype if they have an A/A genotype. For COMT, patients are identified as having an active phenotype if they have the val/val genotype and a less active phenotype if they have val/met or met/met genotype.

After identifying a phenotype associated with the patient's genotype for each gene within the panel, the phenotypes are combined into a combined phenotype, which reflects the phenotype associated with the genotype for each gene within the panel. For example, a combined phenotype for a patient can be: DRD4 positive, SLC6A3 positive, SLC6A2 positive, COMT active, and CYP2D6 phenotype 1.

An algorithm can be used to select the most appropriate medications for an individual patient using a set of rules based on the combined phenotype. Variations in each of the genes are quantitatively considered in the decision-making algorithm. The selection of an appropriate medication is enhanced by including both target data and data related to drug metabolism. This can determine the impact of the CYP products on the clinical response of a particular patient. For example, inclusion of target data and data related to drug metabolism provides the amount of available drug, the ability of the patient to utilize the drug, and information about the quality of the receptor target of the drug, providing a rational approach to selection of medication.

An example of this process would be the selection of an appropriate ADHD medication for a given patient. If the combined phenotype is DRD4 positive, SLC6A3 positive, SLC6A2 positive, COMT active, and CYP2D6 phenotype 1, the algorithm would output methylphenidate (MPH) as the selected medication. If the combined phenotype is DRD4 negative, SLC6A3 positive, SLC6A2 positive, COMT active, and CYP2D6 phenotype 1, the algorithm would output MPH as the selected medication. If the combined phenotype is DRD4 positive, SLC6A3 negative, SLC6A2 positive, COMT active, and CYP2D6 phenotype 1, the algorithm would output MPH as the selected medication. If the combined phenotype is DRD4 negative, SLC6A3 negative, SLC6A2 positive, COMT active, and CYP2D6 phenotype 1, the algorithm would output MPH as the selected medication. If the combined phenotype is DRD4 positive, SLC6A3 positive, SLC6A2 negative, COMT active, and CYP2D6 phenotype 1, the algorithm would output MPH as the selected medication. If the combined phenotype is DRD4 negative, SLC6A3 positive, SLC6A2 negative, COMT active, and CYP2D6 phenotype 1, the algorithm would output MPH as the selected medication. If the combined phenotype is DRD4 positive, SLC6A3 negative, SLC6A2 negative, COMT active, and CYP2D6 phenotype 1, the algorithm would output MPH as the selected medication. If the combined phenotype is DRD4 negative, SLC6A3 negative, SLC6A2 negative, COMT active, and CYP2D6 phenotype 1, the algorithm would output MPH as the selected medication. If the combined phenotype is DRD4 positive, SLC6A3 positive, SLC6A2 positive, COMT active, and CYP2D6 phenotype 2, the algorithm would output MPH as the selected medication. If the combined phenotype is DRD4 negative, SLC6A3 positive, SLC6A2 positive, COMT active, and CYP2D6 phenotype 2, the algorithm would output MPH as the selected medication. If the combined phenotype is DRD4 positive, SLC6A3 negative, SLC6A2 positive, COMT active, and CYP2D6 phenotype 2, the algorithm would output MPH as the selected medication. If the combined phenotype is DRD4 negative, SLC6A3 negative, SLC6A2 positive, COMT active, and CYP2D6 phenotype 2, the algorithm would output MPH as the selected medication. If the combined phenotype is DRD4 positive, SLC6A3 positive, SLC6A2 negative, COMT active, and CYP2D6 phenotype 2, the algorithm would output MPH as the selected medication. If the combined phenotype is DRD4 negative, SLC6A3 positive, SLC6A2 negative, COMT active, and CYP2D6 phenotype 2, the algorithm would output MPH as the selected medication. If the combined phenotype is DRD4 positive, SLC6A3 negative, SLC6A2 negative, COMT active, and CYP2D6 phenotype 2, the algorithm would output MPH as the selected medication. If the combined phenotype is DRD4 negative, SLC6A3 negative, SLC6A2 negative, COMT active, and CYP2D6 phenotype 2, the algorithm would output amphetamines or atomoxetine as the selected medication. If the combined phenotype is DRD4 positive, SLC6A3 positive, SLC6A2 positive, COMT active, and CYP2D6 phenotype 3, the algorithm would output MPH as the selected medication. If the combined phenotype is DRD4 negative, SLC6A3 positive, SLC6A2 positive, COMT active, and CYP2D6 phenotype 3, the algorithm would output MPH as the selected medication. If the combined phenotype is DRD4 positive, SLC6A3 negative, SLC6A2 positive, COMT active, and CYP2D6 phenotype 3, the algorithm would output MPH as the selected medication. If the combined phenotype is DRD4 negative, SLC6A3 negative, SLC6A2 positive, COMT active, and CYP2D6 phenotype 3, the algorithm would output MPH as the selected medication. If the combined phenotype is DRD4 positive, SLC6A3 positive, SLC6A2 negative, COMT active, and CYP2D6 phenotype 3, the algorithm would output MPH as the selected medication. If the combined phenotype is DRD4 negative, SLC6A3 positive, SLC6A2 negative, COMT active, and CYP2D6 phenotype 3, the algorithm would output MPH as the selected medication. If the combined phenotype is DRD4 positive, SLC6A3 negative, SLC6A2 negative, COMT active, and CYP2D6 phenotype 3, the algorithm would output MPH as the selected medication. If the combined phenotype is DRD4 negative, SLC6A3 negative, SLC6A2 negative, COMT active, and CYP2D6 phenotype 3, the algorithm would output amphetamines or atomoxetine as the selected medication. If the combined phenotype is DRD4 positive, SLC6A3 positive, SLC6A2 positive, COMT less active, CYP2D6 phenotype 1, the algorithm would output MPH as the selected medication. If the combined phenotype is DRD4 negative, SLC6A3 positive, SLC6A2 positive, COMT less active, and CYP2D6 phenotype 1, the algorithm would output MPH as the selected medication. If the combined phenotype is DRD4 positive, SLC6A3 negative, SLC6A2 positive, COMT less active, and CYP2D6 phenotype 1, the algorithm would output MPH as the selected medication. If the combined phenotype is DRD4 negative, SLC6A3 negative, SLC6A2 positive, COMT less active, and CYP2D6 phenotype 1, the algorithm would output MPH as the selected medication. If the combined phenotype is DRD4 positive, SLC6A3 positive, SLC6A2 negative, COMT less active, and CYP2D6 phenotype 1, the algorithm would output MPH as the selected medication. If the combined phenotype is DRD4 negative, SLC6A3 positive, SLC6A2 negative, COMT less active, and CYP2D6 phenotype 1, the algorithm would output MPH as the selected medication. If the combined phenotype is DRD4 positive, SLC6A3 negative, SLC6A2 negative, COMT less active, and CYP2D6 phenotype 1, the algorithm would output MPH as the selected medication. If the combined phenotype is DRD4 negative, SLC6A3 negative, SLC6A2 negative, COMT less active, and CYP2D6 is phenotype 1, the algorithm would output low dose atomoxetine as the selected medication. If the combined phenotype is DRD4 positive, SLC6A3 positive, SLC6A2 positive, COMT less active, and CYP2D6 phenotype 2, the algorithm would output MPH as the selected medication. If the combined phenotype is DRD4 negative, SLC6A3 positive, SLC6A2 positive, COMT less active, and CYP2D6 phenotype 2, the algorithm would output MPH as the selected medication. If the combined phenotype is DRD4 positive, SLC6A3 negative, SLC6A2 positive, COMT less active, and CYP2D6 phenotype 2, the algorithm would output MPH as the selected medication. If the combined phenotype is DRD4 negative, SLC6A3 negative, SLC6A2 positive, COMT less active, and CYP2D6 phenotype 2, the algorithm would output amphetamines or atomoxetine as the selected medication. If the combined phenotype is DRD4 positive, SLC6A3 positive, SLC6A2 negative, COMT less active, and CYP2D6 phenotype 2, the algorithm would output MPH as the selected medication. If the combined phenotype is DRD4 negative, SLC6A3 positive, SLC6A2 negative, COMT less active, and CYP2D6 phenotype 2, the algorithm would output amphetamines or atomoxetine as the selected medication. If the combined phenotype is DRD4 positive, SLC6A3 negative, SLC6A2 negative, COMT less active, and CYP2D6 phenotype 2, the algorithm would output amphetamines or atomoxetine as the selected medication. If the combined phenotype is DRD4 negative, SLC6A3 negative, SLC6A2 negative, COMT less active, CYP2D6 phenotype 2, the algorithm would output amphetamines or atomoxetine as the selected medication. If the combined phenotype is DRD4 positive, SLC6A3 positive, SLC6A2 positive, COMT less active, and CYP2D6 phenotype 3, the algorithm would output MPH as the selected medication. If the combined phenotype is DRD4 negative, SLC6A3 positive, SLC6A2 positive, COMT less active, and CYP2D6 phenotype 3, the algorithm would output amphetamines or atomoxetine as the selected medication. If the combined phenotype is DRD4 positive, SLC6A3 negative, SLC6A2 positive, COMT less active, and CYP2D6 phenotype 3, the algorithm would output amphetamines or atomoxetine as the selected medication. If the combined phenotype is DRD4 negative, SLC6A3 negative, SLC6A2 positive, COMT less active, and CYP2D6 phenotype 3, the algorithm would output amphetamines or atomoxetine as the selected medication. If the combined phenotype is DRD4 positive, SLC6A3 positive, SLC6A2 negative, COMT less active, and CYP2D6 phenotype 3, the algorithm would output amphetamines or atomoxetine as the selected medication. If the combined phenotype is DRD4 negative, SLC6A3 positive, SLC6A2 negative, COMT less active, and CYP2D6 phenotype 3, the algorithm would output amphetamines or atomoxetine as the selected medication. If the combined phenotype is DRD4 positive, SLC6A3 negative, SLC6A2 negative, COMT less active, and CYP2D6 phenotype 3, the algorithm would output amphetamines or atomoxetine as the selected medication. If the combined phenotype is DRD4 negative, SLC6A3 negative, SLC6A2 negative, COMT less active, and CYP2D6 phenotype 3, the algorithm would output amphetamines or atomoxetine as the selected medication.

Similar algorithms can be used based on a set of rules relating to six genes (e.g., CYP2D6 gene, the COMT gene, SLC6A2 gene, SLC6A3 gene, DRD4 gene, and one of SLC6A4 gene, a SNAP25 gene, and an ADRA2A gene), or based on a set of rules relating to seven or eight genes (e.g., CYP2D6 gene, the COMT gene, SLC6A2 gene, SLC6A3 gene, DRD4 gene, and two or three of SLC6A4 gene, a SNAP25 gene, and an ADRA2A gene).

In some embodiments, the algorithmic analysis can be designed to place the medications in three categories: 1) medications that are acceptable for use, i.e., the medication has a high probability of normal metabolism within an individual having a particular genotype, 2) medications that can be used with caution (e.g., medication may require some dosing adjustment based on atypical metabolism); and 3) medications that should be avoided or used with caution and monitoring, e.g., due to potential difficulties in dosing.

Data related to the medication response of first- and second-degree relatives of the patient can be entered into the algorithmic equation, which pertains to the medication selection of drugs in the first category that has been identified. An adjustment of the rank-ordered, appropriate medications then can be calculated based on clinical responses by family members.

Output from the algorithm also can be integrated with historical data. For example, if a family member had responded well to a particular medication, this would confirm that the medication is acceptable for use, or, if a first or second degree relative had a problematic response to this medication, an alternative could be chosen.

Computer Systems

Techniques described herein can be implemented in a computer system having a processor that executes specific instructions in a computer program. The computer system may be arranged to output a medication profile based on receiving a patient's genotype. Particularly, the computer program may include instructions for the system to select the most appropriate medication (e.g., a psychostimulant or non-stimulant medication) for an individual patient.

The following are examples of features that may be included in a system. The computer program may be configured such that the computer system can identify the phenotype based on received data and provide a preliminary identification of the universe of possible medications. The system may be able to rank-order the identified medications based on specific co-factors in the algorithmic equation. The system may be able to adjust the rank ordering based on the genotypic polymorphism(s) carried by the patient. The system may be able to adjust the rank ordering based on clinical responses, such as by family members of the patient.

FIG. 1 is a block diagram of a computer system 100 that can be used in the operations described above, according to one embodiment. The system 100 includes a processor 110, a memory 120, a storage device 130 and an input/output device 140. Each of the components 110, 120, 130 and 140 are interconnected using a system bus 150. The system may include analyzing equipment 160 for determining the patient's genotype.

The processor 110 is capable of processing instructions for execution within the system 100. In one embodiment, the processor 110 is a single-threaded processor. In another embodiment, the processor 110 is a multi-threaded processor. The processor 110 is capable of processing instructions stored in the memory 120 or on the storage device 130, including for receiving or sending information through the input/output device 140.

The memory 120 stores information within the system 100. In one embodiment, the memory 120 is a computer-readable medium. In one embodiment, the memory 120 is a volatile memory unit. In another embodiment, the memory 120 is a non-volatile memory unit.

The storage device 130 is capable of providing mass storage for the system 100. In one embodiment, the storage device 130 is a computer-readable medium. In various different embodiments, the storage device 130 may be a floppy disk device, a hard disk device, an optical disk device, or a tape device.

The input/output device 140 provides input/output operations for the system 100. In one embodiment, the input/output device 140 includes a keyboard and/or pointing device. In one embodiment, the input/output device 140 includes a display unit for displaying graphical user interfaces.

Figure 2:
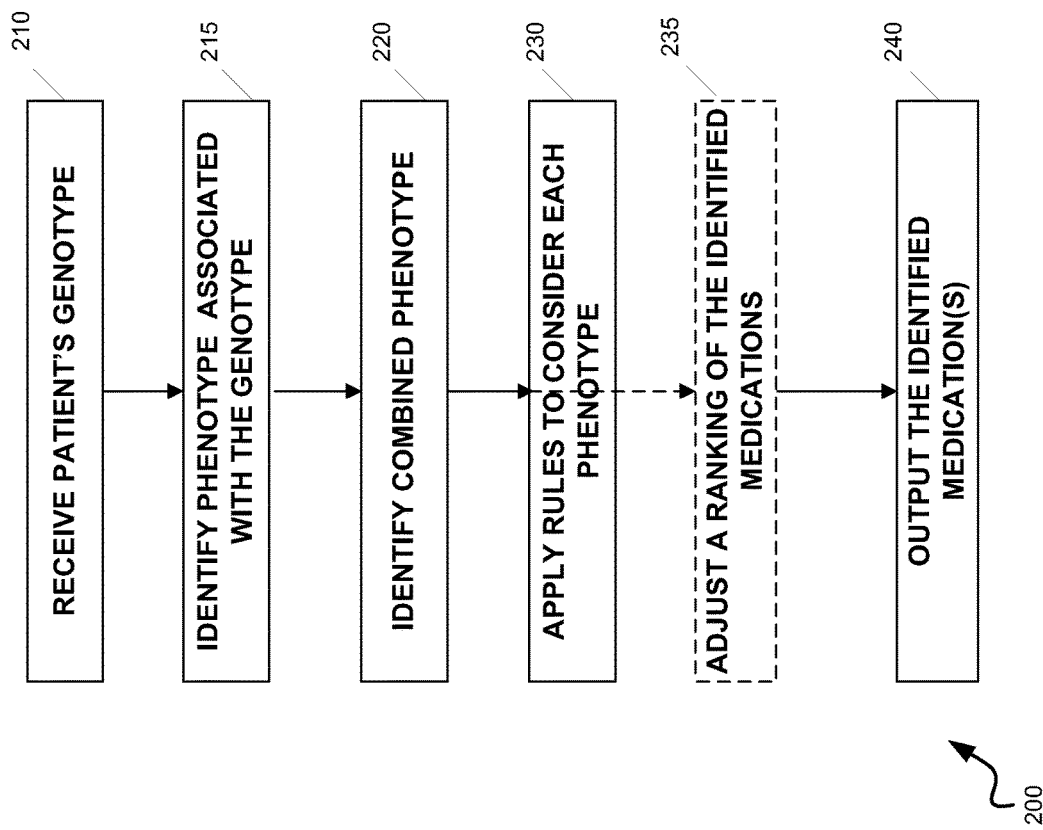
FIG. 2 is a flow chart of a method 200 for selecting a medication for a patient.

The system 100 may be used for selecting a medication. FIG. 2 shows a flow chart of a method 200 of selecting a medication for a patient. Preferably, the method 200 is performed in the system 100. For example, a computer program product can include instructions that cause the processor 110 to perform the steps of the method 200. The method 200 includes the following steps.

Receiving, in step 210, a patient's genotype for a panel of genes. The genotype may be entered by a user via input/output device 140. For example, the user may obtain the patient's genotype for a panel of genes using the analyzing equipment 160 (which may or may not be connected to the system 100). The user may type the patient's genotype on input/output device 140, such as a keyboard, for receipt by the system 100.

The genotype may be received directly from the analyzing equipment 160. For example, analyzing equipment 160 may include a processor and suitable software such that it can communicate over a network. The system 100 may be connected to the analyzing equipment 160 through input/output device 140, such as a network adapter, and directly receive the patient's genotype.

Identifying, in step 215, a phenotype 180 that is associated with the genotype 170 of each gene within the panel of genes. For example, the system 100 may perform a database search in the storage device 130.

Combining, in step 220, each phenotype 180 into a combined phenotype 190 for the patient.

Applying, in step 230, a set of rules (e.g., as discussed above) to quantitatively consider each phenotype of the combined phenotype 190 to select the appropriate medication or medications 195. Optional step 235 will be described below.

Outputting, in step 240, the identified medication or medications 195 in response to receiving the patient's genotype and applying the rules to consider the combined phenotype. The system may output the identified medication or medications 195 through input/output device 140. For example, the identified medication may be printed or displayed in a suitable graphical user interface on a display device. As another example, the system 100 may transmit the identified medication over a network, such as a local area network or the Internet, to which the input/output device 140 is connected.

The format of the medication(s) 195 outputted by system 100 can be flexible. For example, the outputted information can include a ranking of several medications. In such implementations, the method 200 may include optional step 235 of adjusting the ranking before outputting the identified medication. For example, the system 100 may adjust the ranking based on the combined phenotype of the patient. As another example, step 235 may involve adjusting the ranking based on a clinical response. The clinical response may be received by the system 100 in the same way as the patient's genotype. For example, the ranking can be adjusted based on a clinical response by a member of the patient's family.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of selecting a medication and treating a patient having ADHD, the method comprising:
  (a) genotyping a biological sample from a patient to determine the patient's genotype for a set of markers of a panel of genes using a method comprising one or more of a polymerase chain reaction (PCR) based nucleic acid amplification step, allele specific hybridization, and allele specific restriction digests, and the set of markers and genes comprising the following:
    (i) one or more cytochrome P450 CYP2D6 alleles selected from the group consisting of *2BD, *3, *4, *5, *6, *7, *8, *9, *10, *11, *12, *15, *17, and *41;
    (ii) the tandem duplication polymorphism in the promoter region of the dopamine receptor DRD4 gene that consists of a 120 base pair allele and a 240 base pair allele;
    (iii) the G1278A polymorphism in exon 9 of the norepinephrine transporter gene SLC6A2;
    (iv) the 10 repeat unit and the 9 repeat unit of the variable number tandem repeat (VNTR) polymorphism in the dopamine transporter gene SLC6A3; and
    (v) the G158A polymorphism in the catechol-O-methyl transferase gene COMT;
  (b) receiving, in a computer system, the patient's genotype determined in (a) and assigning a phenotype for each gene based on the patient's genotype as follows:
    a CYP2D6 phenotype selected from phenotype 1, phenotype 2 and phenotype 3, wherein a homozygous or compound heterozygous genotype for any of the alleles in (i) is assigned phenotype 1, a heterozygous genotype for any of the alleles in (i) is assigned phenotype 2, and a genotype lacking any of the alleles in (i) is assigned phenotype 3;
    a DRD4 phenotype selected from a positive phenotype if the genotype is homozygous for the rare 120 allele and a negative phenotype if the common 240 allele is present;
    a SLC6A3 phenotype selected from a positive phenotype if the genotype is homozygous for the 10 repeat unit and a negative phenotype if the 9 repeat unit is present;
    a SLC6A2 phenotype selected from a positive phenotype if the genotype is G/A or G/G and a negative phenotype if the genotype is A/A;
    a COMT phenotype selected from an active phenotype if the genotype is val/val and a less active phenotype if the genotype is val/met or met/met;
  (c) combining, using said computer system, each assigned phenotype for each gene of the panel of genes into a combined phenotype for the patient;
  (d) applying a set of rules to select a medication for the patient based upon the patient's combined phenotype;

(e) outputting the selection of medication according to the patient's combined phenotype as follows:

the patient has a combined phenotype selected from:

(i) DRD4 negative phenotype; SLC6A3 negative phenotype; SLC6A2 negative phenotype; COMT active phenotype; CYP2D6 phenotype 2;

(ii) DRD4 negative phenotype; SLC6A3 negative phenotype; SLC6A2 negative phenotype; COMT active phenotype; CYP2D6 phenotype 3;

(iii) DRD4 negative phenotype; SLC6A3 negative phenotype; SLC6A2 positive phenotype; COMT less active phenotype; CYP2D6 phenotype 2;

(iv) DRD4 negative phenotype; SLC6A3 positive phenotype; SLC6A2 negative phenotype; COMT less active phenotype; CYP2D6 phenotype 2;

(v) DRD4 positive phenotype; SLC6A3 negative phenotype; SLC6A2 negative phenotype; COMT less active phenotype; CYP2D6 phenotype 2;

(vi) DRD4 negative phenotype; SLC6A3 negative phenotype; SLC6A2 negative phenotype; COMT less active phenotype; CYP2D6 phenotype 2;

(vii) DRD4 negative phenotype; SLC6A3 positive phenotype; SLC6A2 positive phenotype; COMT less active phenotype; CYP2D6 phenotype 3;

(viii) DRD4 positive phenotype; SLC6A3 negative phenotype; SLC6A2 positive phenotype; COMT less active phenotype; CYP2D6 phenotype 3;

(ix) DRD4 negative phenotype; SLC6A3 negative phenotype; SLC6A2 positive phenotype; COMT less active phenotype; CYP2D6 phenotype 3;

(x) DRD4 positive phenotype; SLC6A3 positive phenotype; SLC6A2 negative phenotype; COMT less active phenotype; CYP2D6 phenotype 3;

(xi) DRD4 negative phenotype; SLC6A3 positive phenotype; SLC6A2 negative phenotype; COMT less active phenotype; CYP2D6 phenotype 3;

(xii) DRD4 positive phenotype; SLC6A3 negative phenotype; SLC6A2 negative phenotype; COMT less active phenotype; CYP2D6 phenotype 3; and (xiii) DRD4 negative phenotype; SLC6A3 negative phenotype; SLC6A2 negative phenotype; COMT less active phenotype; CYP2D6 phenotype 3;

and the output is amphetamines or atomoxetine; or the patient has a combined phenotype that is: DRD4 negative phenotype; SLC6A3 negative phenotype; SLC6A2 negative phenotype; COMT less active phenotype; CYP2D6 phenotype 1; and the output is low dose atomoxetine; and (f) administering to the patient a medication selected from amphetamines, atomoxetine, or low dose atomoxetine according to the output for the patient's combined phenotype in step (e), thereby treating the ADHD in the patient.

2. The method of claim 1, wherein the patient's genotype is received directly from equipment used in determining the patient's genotype.

3. The method of claim 1, wherein a user enters the patient's genotype in the computer system.

4. The method of claim 1, wherein the medication administered to the patient is an amphetamine.

5. The method of claim 4, wherein the amphetamine administered to the patient is a long acting amphetamine.

6. The method of claim 5, wherein said long acting amphetamine is selected from the group consisting of a dextroamphetamine spansule preparation, an extended release amphetamine salt preparation, and a lisdexamphetamine preparation.

7. The method of claim 4, wherein the amphetamine administered to the patient is a short acting amphetamine selected from the group consisting of dextroamphetamine sulfate preparation, an amphetamine salt preparation of dextroamphetamine and amphetamine, and methamphetamine.

8. The method of claim 1, wherein the medication administered to the patient is atomoxetine.

9. The method of claim 1, wherein said biological sample is a saliva sample or peripheral blood sample.

* * * * *